United States Patent
Suryadevara et al.

[11] Patent Number: 5,843,574
[45] Date of Patent: Dec. 1, 1998

[54] POLYAMIDE SUTURE HAVING IMPROVED TENSILE STRENGTH

[75] Inventors: Jogendra Suryadevara, Franklin Park; Irandokht Irene Nozad, Branchburg, both of N.J.

[73] Assignee: Ethicon, Inc., Somerville, N.J.

[21] Appl. No.: 977,938

[22] Filed: Nov. 24, 1997

Related U.S. Application Data

[60] Continuation of Ser. No. 466,301, Jun. 6, 1995, abandoned, which is a division of Ser. No. 226,138, Apr. 11, 1994, Pat. No. 5,571,469.

[51] Int. Cl.⁶ .............................. D02G 3/00; A61B 17/04
[52] U.S. Cl. .......................... 428/364; 428/395; 606/228
[58] Field of Search ..................... 428/364, 395, 428/375; 606/228; 525/66

[56] References Cited

U.S. PATENT DOCUMENTS

| | | | |
|---|---|---|---|
| 2,212,772 | 8/1940 | Graves | 264/178 F X |
| 2,226,529 | 12/1940 | Austin | 264/289.6 X |
| 3,791,388 | 2/1974 | Hunter et al. | 606/229 |
| 4,009,511 | 3/1977 | Gauntt | 264/25 |
| 4,338,277 | 7/1982 | Saito et al. | 264/235.6 |
| 4,578,451 | 3/1986 | Weaver et al. | 528/292 |
| 4,621,638 | 11/1986 | Silverstrini | 606/230 |
| 4,909,976 | 3/1990 | Cuculo et al. | 264/211.15 |
| 5,082,610 | 1/1992 | Fish et al. | 264/80 |
| 5,102,419 | 4/1992 | Gertzman et al. | 606/228 |
| 5,102,420 | 4/1992 | Hunter et al. | 428/375 |
| 5,122,569 | 6/1992 | Scheibelhoffer et al. | 525/66 |
| 5,212,238 | 5/1993 | Scheibelhoffer et al. | 525/66 |
| 5,279,783 | 1/1994 | Li et al. | 264/178 F |
| 5,349,044 | 9/1994 | Lie et al. | 606/228 |
| 5,378,538 | 1/1995 | Makino et al. | 428/364 |
| 5,442,032 | 8/1995 | Arnold et al. | 428/395 |

FOREIGN PATENT DOCUMENTS

| | | |
|---|---|---|
| 0350945 | 1/1990 | European Pat. Off. ......... D01D 5/16 |
| 350 945 | 1/1990 | European Pat. Off. . |
| 0415783 | 3/1991 | European Pat. Off. ....... D01D 10/92 |
| 415 783 | 3/1991 | European Pat. Off. . |
| 0423806 | 4/1991 | European Pat. Off. .......... D02J 1/22 |
| 423 806 | 4/1991 | European Pat. Off. . |
| 0477020 | 3/1992 | European Pat. Off. ........ A61B 17/12 |
| 477 020 | 3/1992 | European Pat. Off. . |
| 553 882 A1 | 8/1992 | European Pat. Off. . |

*Primary Examiner*—Newton Edwards
*Attorney, Agent, or Firm*—Hal Brent Woodrow

[57] ABSTRACT

The present invention provides a new polyamide suture and a process for manufacturing this suture. The suture is made by melt extruding, quenching and drawing a polyamide filament. The polyamide filament is then wound on racks and annealed at a temperature of from about 120° C. to about 185° C. for at least 30 minutes. The sutures produced by this process have improved knot strength, tensile strength and stability.

8 Claims, 2 Drawing Sheets

POLYAMIDE SUTURE HAVING IMPROVED TENSILE STRENGTH

This is a continuation of Ser. No. 08/466,301 filed Jun. 6, 1995, now abandoned, which is a division of application Ser. No. 08/226,138, filed Apr. 11, 1994, now U.S. Pat. No. 5,571,469, which is hereby incorporated by reference.

FIELD OF THE INVENTION

This invention relates to a polyamide suture and a process for producing a polyamide suture. More particularly this invention relates to a polyamide suture with improved knot and tensile strength and structural stability and a process for making this polyamide suture.

BACKGROUND OF THE INVENTION

Many patents describe processes for manufacturing fibers from polyamide polymers. U.S. Pat. No. 2,212,772 describes the preparation of fibers such as bristles, sutures, fishing lines and the like from polyamides polymers. The process described in this patent consists of extruding the fiber then rapidly cooling the fiber in a liquid quenching bath to improve the fiber's drawability. Later patents describe processes for making heavy denier polyamide fibers used as the tire reinforcement (such as described in U.S. Pat. No. 4,009,511) or fishing lines (such as described in U.S. Pat. No. 4,338,277 and U.S. Pat. No. 5,082,610). Unfortunately, these later processes are not readily adapted to the production of sutures.

Sutures, unlike the tire cords and fishing lines described above, require a unique combination of physical properties. Ideally, polyamide sutures must be nonirritating, flexible, with high tensile strength and knot strength. Additionally, sutures must retain their physical properties after conventional processing such as dyeing, sterilization and resterilization. Obtaining the desired combination of physical properties is further complicated by the fact that polyamide sutures commonly are produced in very small diameter filaments. For example, the nylon sutures commonly used in ophthalmic surgery, have a diameter of only 20–29 microns.

Currently, polyamide sutures are produced by extruding a polyamide polymer through a spinnerette into a quenching medium then drawing the resultant fiber to obtain the desired degree of orientation. The sutures are then dyed to the desired color, attached to needles, packaged and sterilized. The sutures may then be sold directly to surgeons, hospitals or suppliers. Often after being sold to hospitals or suppliers the sutures are repackaged in surgical kits and resterilized.

Although the polyamide sutures produced as described above have acceptable physical properties, it would be desirable to improve these sutures. Thus it is an object of the present invention to provide polyamide sutures with improved tensile strengths and greater resistance to suture degradation during dyeing, sterilization and resterilization. Another object of the present invention is to provide a process for making polyamide sutures with improved tensile strengths and greater resistance to suture degradation during dyeing, sterilization and resterilization.

SUMMARY OF THE INVENTION

We have discovered an improved polyamide suture comprising a polyamide suture having a tensile strength of greater than 130 KPSI.

We have also discovered a process for manufacturing a fine denier polyamide filament suitable for use in a suture comprising extruding a polyamide under conditions suitable to provide a filament; quenching in a controlled environment to provide a quenched filament; drawing the quenched filament at a draw ratio of from about 3.0 to about 5.5× to provide a drawn filament; then annealing said drawn filament at a temperature of from about 120° C. to about 185° C. for in the range of from about 30 minutes to about 8 hours.

DETAILED DESCRIPTION OF THE INVENTION

Figure 1:
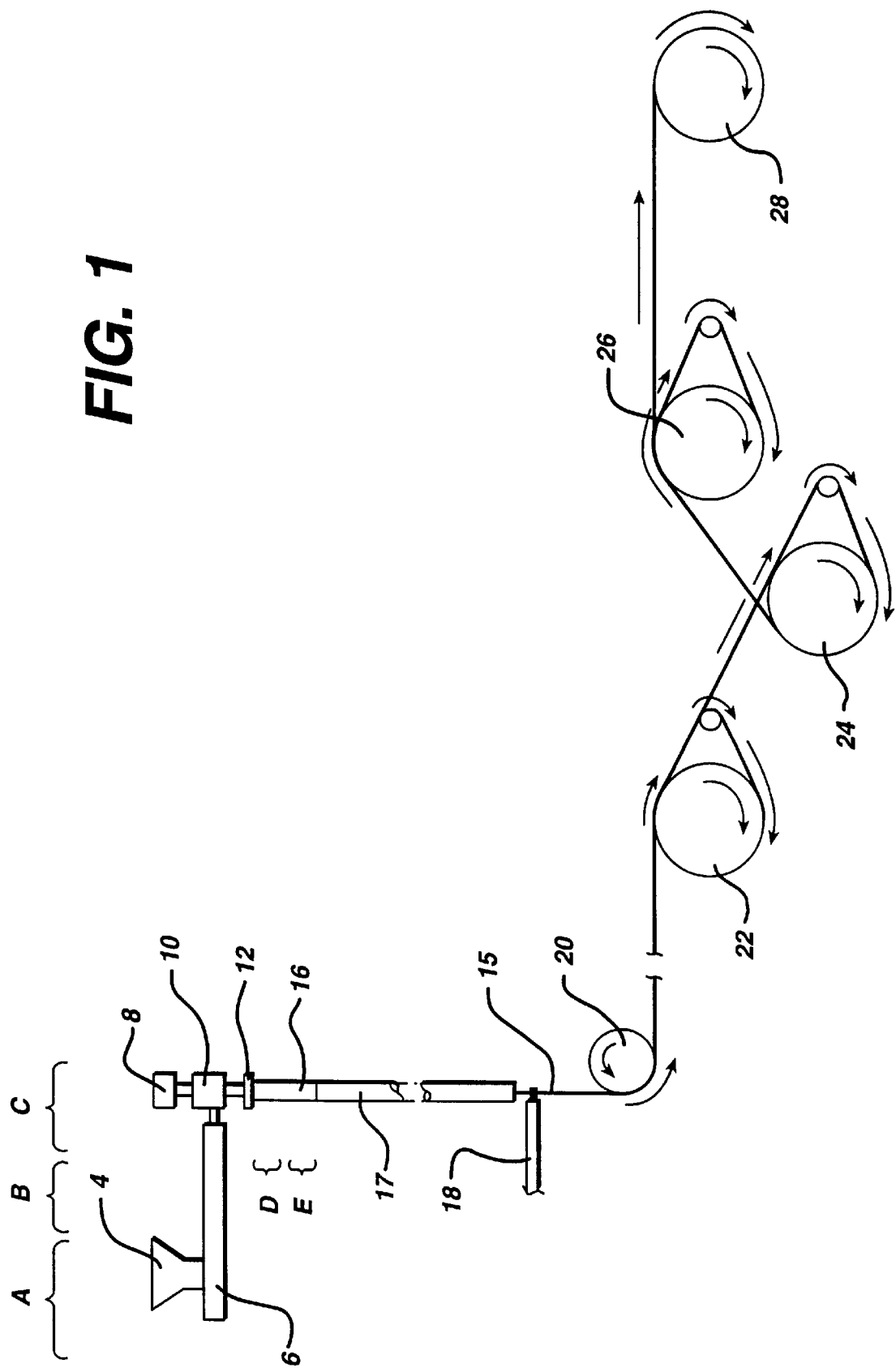
FIG. 1 is a schematic illustration of the extrusion, quenching and drawing of a polyamide suture.

The present invention provides a novel polyamide suture and a process for manufacturing this suture. The novel polyamide suture provided by the present invention is a significant improvement over previously produced sutures. The inventive sutures have increased strength and improved stability, which allows the sutures to be sterilized and resterilized without significant losses in its tensile and knot strengths. The process is well suited for manufacturing fine denier sutures, particularly sutures in sizes from about 7/0 to about 11/0 (about 69 to about 10 microns). The process comprises four separate steps. First, a polyamide polymer is extruded into a filament. Second, the filament is quenched in a controlled environment. Third, the quenched filament is drawn from about 3× to about 5.5× its original length. Fourth, the filament is annealed at a temperature from about 120° C. to about 185° C. for a period of time sufficient to optimize the filament's crystallinity. The heat may be applied as dry heat preferably at a temperature from about 140° C. to about 185° C. or in the form of moist heat preferably at a temperature from about 120° C. to about 160° C. Generally the filament will be exposed to these temperatures in the range of from about 30 minutes to about 8 hours and preferably the filament will be exposed to these temperatures in the range of from about 2 hours to about 4 hours.

The sutures produced by the present process have improved stability, knot strength and tensile strength compared to sutures previously available. The filaments produced by the inventive process are particularly well suited for use as sutures because of their resistance to strength loss due to sterilization and resterilization.

As shown in Example 2, the inventive sutures with an I.V. of 1.5 generally retained higher knot strengths and greater percent elongations after sterilization and resterilization as compared to sutures produced by conventional processes. Sutures produced by the process of this invention will have a tensile strength greater than 130 KPSI and preferably in the range of from about 132 KPSI to about 145 KPSI and most preferably in the range of from about 134 KPSI to about 145 KPSI.

For example the percent crystallinity of a nylon 6 and nylon 66 sutures may be 10 percent greater than the crystallinity of sutures produced without annealing. Preferably the annealing will be controlled to provide a crystallinity of in the range of greater than 40 percent to about 46 percent crystallinity and most preferably the crystallinity will be in the range of from 42 to 46 percent for nylon 6 filaments. Preferably the crystalline structure of the crystalline regions will be predominantly alpha crystals. The alpha crystals contained in the inventive suture also will preferably have predominantly a fine crystal texture meaning as determined by wide angle X-ray diffraction the crystalline size will average less than 60 angstroms in crystalline breath.

Theoretically, but in no way limiting the scope of this invention, the changes in crystalline structure are believed to improve sutures due to a variety of effects. First, the alpha crystalline morphology is believed to be the most stable crystallite structure, which enhances the sutures resistance to crystallite changes that might weaken the filament. Further the fine texture of the crystals in the sutures also directly affects the sutures' knot strength and elongation properties. The improved stability conferred by the fine texture of the inventive sutures can clearly be seen in the strength and elongation data presented on I.V. 1.5 nylon 6 sutures after ethylene oxide resterilization presented in Example 2 and the DMS data presented in FIG. 2. Therefore, it is believed that by annealing filaments under appropriate conditions that an improved crystalline morphology may be produced.

Any nontoxic, substantially nonirritating polyamides may be used in the practice of the present invention. These include, but are not limited to homopolymers such as polyhexamethylene adipamide (nylon 66), polyhexamethylene sebacamide (nylon 610), polycapramide (nylon 6), polydodecanamide (nylon 12) and polyhexamethylene isophthalamide (nylon 61) and the like. Also included are copolymers and blended polymers thereof. Currently preferred are homopolymers of nylon 66 and nylon 6.

Suitable polyamides should have a weight average molecular weight of from about 30,000 to about 55,000. Most preferably, the polyamides used to make sutures will have a high weight average molecular weight that is defined for this application to be a weight average molecular weight from about 48,000 to about 55,000. High weight average molecular weight polymers are preferred for manufacturing sutures to increase the overall strength of the suture filament.

The polyamide polymer is generally provided in the form of pellets or powder. The moisture content of the polymer used in the present invention should be less than 0.03 percent by weight. The polyamide polymer is then extruded through a conventional extruder with an appropriate size spinnerette to provide one or more filaments. For producing sutures with very small cross-sectional areas, the polyamide filament is quenched in a controlled environment. The controlled environment may have one or more temperature zones at specific temperatures to improve the toughness of the filament. One suitable means of providing a controlled environment is to use a chimney with heating elements. For example, nylon 6 is preferably maintained at temperature of from about 480° F. to about 550° F. by extruding the filament through a chimney of in the range of from about 8 to about 20 inches (about 20 to about 50 cm) in length. After the polyamide filament exits the chimney, it may cooled (quenched) to room temperature by exposure to the atmosphere or immersion in water. For ease of manufacturing the exposure to the atmosphere should occur in a chute.

The polyamide filament is then oriented by drawing the filament. The drawing conditions will, of course, vary with the particular polymer used and the tensile strength properties desired. Generally, the polyamide filaments should be drawn in one or more steps in the range of from about 3.0 to about 5.5×, preferably the filaments will be drawn 3.8 to 4.2× and most preferably 4×. A single step drawing process usually utilizes 2–3 rolls or godets operating at progressively faster rotational speeds to draw the filament. It is preferred for the practice of the present invention to draw the filament between two rolls and to heat the second roll to a temperature in the range of from about 155° F. to about 225° F. and preferably in the range of from 175° F. to 195° F. The drawn filament is then wound on a take-up spindle for storage or transfer for immediate processing.

It is preferred for the practice of this invention to transfer the filament from a spindle to a rack. By mounting the filament on the rack under uniform tension the filaments produced by the present invention will have greater uniformity of properties and avoid acquiring dents and kinks.

The filament is then annealed by placing the filament in an oven that provides substantially uniform heat to the filaments. The time and temperature at which a particular filament is annealed may be optimized by monitoring the morphology of the suture by following the percent crystallinity, dynamic mechanical stress response and crystalline texture of the filament. Annealing at too high a temperature will destroy the filament's orientation. Annealing at too low a temperature will result in insufficient crystallization. Generally, a filament of nylon 6 will be annealed by placing the filament in an oven at a temperature in the range of from about 120° C. to 185° C. The filament of nylon 6 should be annealed in the ovens in the range of from about 30 minutes to about 8 hours and preferably in the range of from about 2 hours to about 4 hours.

The annealing of polyamide filaments is critical for the manufacture of fine size sutures. This step of the process is believed to improve the crystalline morphology in small diameter sutures, which substantially improves the stability of these sutures.

After the annealing step, the suture filaments may be dyed, attached to needles, packaged and sterilized using conventional techniques. The suture is preferably dyed while still on the rack to avoid dents and the like.

The sutures produced by the process described above have significantly improved stability and if a higher molecular weight polyamide is used will have improved knot strengths. Using the inventive process with a high molecular weight polyamide polymers significantly improves the properties of size 7/0 to 11/0 sutures. These sutures can be used as monofilament sutures or can be made into braided multifilament sutures. Example 4 provides a comparison of a conventionally produced suture to the inventive suture.

Referring to FIG. 1, dried polyamide pellets (or powder) are first loaded in hopper 4 of the barrel 6. The polyamide is heated in the barrel extruder 6. A metered amount of melted polyamide is forced through the spin pack 10 at a controlled pressure by a metering pump 8. The molten polyamide passes through the holes in spinnerette 12 and enters chimney 16. Chimney 16 is designed to air quench the extruded filament in a controlled environment. Chimney 16 is generally 8 to 20 inches (20 to 50 cm) in length. The filament 15 exits the chimney and enters chute 17 were it cools to substantially room temperature. As the filament 15 exits chute 17 it may be lubricated at this point by a lubricating device 18. The filament then passes under drive roller and is fed to orientation roll 22. The filament 17 is wrapped several times around orientation roll 22. From the orientation roll 22 the filament then proceeds to heated roll 24. The relative speeds of the orientation roll 22 and the heated roll 24 are adjusted to provide a draw ratio of from about 3 to about 5.5×. The filament is wrapped several times around the heated roll 24. The heated roll 24 is maintained at an elevated temperature in the range of from about 140° C. to about 205° C. The filament is then fed to a let down roll 26, which is rotated at a speed sufficient to maintain tension on the filament. The filament then is collected on a take-up spool 28. The filament is then placed on a rack, such as the rack described in U.S. Pat. No. 3,630,205 to Gregory J. Listner (hereby incorporated by reference) and annealed.

The following non-limiting examples are provided to further illustrate the practice of the present invention.

EXAMPLE I

This example describes the manufacture of a 10/0 suture using the inventive process. The polyamide used in this process was nylon 6 with a molecular weight of about 49,000 and an intrinsic viscosity of 1.775. The nylon 6 was dried to a moisture content of less than 0.03 percent by weight before use and held under a vacuum until added to the extruder.

The filaments were made under the following conditions:

TABLE 1

10/0 NYLON EXTRUSION AND ORIENTATION CONDITIONS AND PHYSICAL PROPERTIES

| TEMPERATURE, °F. | |
|---|---|
| FEED | 430 |
| TRANSITION | 437 |
| BLENDER | 460 |
| PUMP | 500 |
| BLOCK | 500 |
| DIE | 514 |
| CHIMN 1 | 530 |
| CHIMN 2 | 530 |
| PRESSURE PSI | |
| BARREL | 1000 |
| PUMP | 5885 |
| SPEED, RPM | |
| SCREW | 18 |
| PUMP | 34.8 |
| ORIENTATION # WRAPS | |
| ORIENTATION ROLL | 5 |
| HEATED ROLL | 25 |
| LET DOWN ROLL | 5 |
| SPEED, FPM | |
| ORIENTATION ROLL | 250 |
| HEATED ROLL | 996 |
| LET OFF ROLL | 1000 |
| DRAW RATIO | 4.0 |
| TEMPERATURE, °F. | |
| ORIENTATION ROLL | AMB |
| HEATED ROLL | 185 |
| LET OFF ROLL | AMB |
| SAMPLE PROPERTIES | |
| # SPOOLS | 4-1 |
| DENIER | 22.0 |
| TENSILE, Kpsi | 154 |
| ELONGATION TO BREAK, % | 37.6 |

The filaments produced by this process were then wound on a rack. The racks were then placed in an annealing oven and annealed at 160° C.

EXAMPLE 2

This example shows the improved properties which sutures have when produced following the inventive process.

Sutures were prepared using two different nylon 6 resins under the conditions specified in Example 1. The first nylon 6 resin had a weight average molecular weight of about 35,000 and an intrinsic viscosity of 1.5. The second nylon 6 resin had a weight average molecular weight of about 49,000 and an intrinsic viscosity of 1.775. The nylon 6 resins were provided in the form of pellets. The nylon 6 pellets were dried to a moisture content of less than 0.03 percent by weight before use and held under vacuum until transferred to the extruder. The extrusion and drawing were performed as described in Example 1. The sutures produced by this process were annealed for 0, 4, 6, and 8 hours. The tensile strength, knot strength and percent elongation were then determined after dyeing, and subsequently after sterilization with cobalt then resterilization with ethylene oxide.

The characteristic properties of the sutures of the invention were determined by conventional test procedures. The tensile properties (i.e., straight and knot tensile strengths and elongation) displayed herein were determined with an INSTRON Tensile Tester. The settings used to determine the straight tensile, knot tensile and break elongation were the following, unless indicated:

TABLE 2

| | GAUGE LENGTH (cm) | CHART SPEED (cm) | CROSSHEADSPEED (ml/min.) |
|---|---|---|---|
| STRAIGHT TENSILE | 12.7 | 30.5 | 30.5 |
| KNOT TENSILE | 12.7 | 30.5 | 30.5 |
| BREAK ELONGATION | 12.7 | 30.5 | 30.5 |

The straight tensile strength was calculated by dividing the force to break by the initial cross-sectional area of the suture. The elongation at break was read directly from the stress-strain curve of the sample.

The knot tensile strength of a suture was determined in separate tests. The surgeon's knot was a square knot in which the free end was first passed twice, instead of once, though the loop, and the ends drawn taut so that a single knot was superimposed upon a compound knot. The first knot was started with the left end over the right end and sufficient tension was exerted to tie the knot securely.

The specimen was placed in the INSTRON Tensile Tester with the knot approximately midway between the clamps. The knot tensile strength was calculated by dividing the force required to break by the initial cross-sectional area of the fiber. The tensile strength values are reported in KPSI ($PSI \times 10^3$).

Table 3 provides the properties of 10/0 sutures of made from nylon 6. Samples 1, 19, 2, 20, 3 and 21 were made with the nylon 6 resin having a weight average molecular weight of 49,000. Samples 7, 25, 8, 26, 9, and 27 were made with the nylon 6 resin having a weight average molecular weight of 37,000.

TABLE 3

| ITM # | HRS | DYED[1] STR KPSI | KNT KPSI | ELG % | CO 60 STERILIZED[2] STR KPSI | KNT KPSI | ELG % | ETO[3] RESTERILIZED STR KPSI | KNT KPSI | ELG % |
|---|---|---|---|---|---|---|---|---|---|---|
| | | | | NYLON 6 MW 49,000 | | | | | | |
| 1 | 0 | 142 | 110 | 34.6 | 130 | 96 | 31.1 | 123 | 92 | 27.1 |
| 19 | 4 | 144 | 106 | 35 | 136 | 118 | 32 | 136 | 108 | 30 |
| 2 | 0 | 137 | 111 | 34.5 | 128 | 98 | 30.5 | 124 | 94 | 25.9 |
| 20 | 6 | 147 | 126 | 33.4 | 134 | 107 | 31.8 | 136 | 108 | 31.1 |
| 3 | 0 | 135 | 111 | 32.9 | 129 | 108 | 32 | 127 | 99 | 26.7 |
| 21 | 8 | 148 | 123 | 34.9 | 132 | 99 | 32 | 140 | 109 | 31.7 |
| | | | | NYLON 6 MW 37,000 | | | | | | |
| 7 | 0 | 131 | 110 | 34.1 | 115 | 94 | 30.3 | 115 | 90 | 25.0 |
| 25 | 4 | 131 | 107 | 34.8 | 123 | 91 | 32.7 | 126 | 105 | 29.7 |
| 8 | 0 | 126 | 102 | 30.3 | 113 | 84 | 27.8 | 110 | 76 | 24.0 |
| 26 | 6 | 138 | 120 | 34.2 | 127 | 103 | 33.2 | 125 | 102 | 28.7 |
| 9 | 0 | 129 | 106 | 29.3 | 116 | 89 | 27.9 | 109 | 77 | 23.5 |
| 27 | 8 | 137 | 112 | 32.2 | 124 | 104 | 31.3 | 127 | 103 | 28.7 |

[1]The sutures were dyed with a logwood dye in an aqueous bath with fixing salts at approximately 210° F.
[2]The sutures were sterilized with gamma irradiation from a cobalt 60 source.
[3]The sutures were resterilized with ethylene oxide.

Table 4 provides the properties of 10/0 sutures made from the nylon 66 resin.

TABLE 4

| ITM # | ANL HRS | DYED[1] STR KPSI | KNT KPSI | ELG % | CO 60 STERILIZED[2] STR KPSI | KNT KPSI | ELG % | ETO[<3] RESTERILIZED STR KPSI | KNT KPSI | ELG % |
|---|---|---|---|---|---|---|---|---|---|---|
| | | | | NYLON 66 | | | | | | |
| 4 | 0 | 112 | 93 | 33.0 | 105 | 88 | 28.7 | 105 | 86 | 26.6 |
| 13 | 4 | 122 | 106 | 31.1 | 107 | 91 | 27.8 | 116 | 92 | 25.7 |
| 5 | 0 | 112 | 97 | 26.0 | 107 | 87 | 24.0 | 107 | 88 | 20.9 |
| 14 | 6 | 123 | 101 | 32.9 | 108 | 93 | 29.6 | 112 | 92 | 27.4 |
| 8 | 0 | 116 | 97 | 25.6 | 101 | 80 | 24.9 | 108 | 85 | 22.2 |
| 15 | 8 | 124 | 86 | 32.8 | 106 | 91 | 27.0 | 111 | 92 | 28.6 |

[1]The sutures were dyed with a logwood dye in an aqueous bath with fixing salts at approximately 210° F.
[2]The sutures were sterilized with gamma irradiation from a cobalt 60 source.
[<3]The sutures were resterilized with ethylene oxide.

Tables 3 and 4 conclusively prove that the sutures produced by the inventive process have improved tensile strength after dyeing and significantly higher knot and tensile strength after sterilization and resterilization.

EXAMPLE 3

This example shows the improved mechanical properties that the inventive sutures possess.

Three different nylon 6 sutures were tested in this experiment. The first and second sutures were made of a nylon 6 polymer with weight average molecular weight respectively of 37,000 and 49,000 prepared as described in Example 1 (identified respectively as Items 19 and 25 in Example 2). The third suture was made of a nylon 6 polymer with a weight average molecular weight of 37,000 prepared as described in Example 1, except the suture was not annealed (identified as Item 7 in Example 2).

Figure 2:
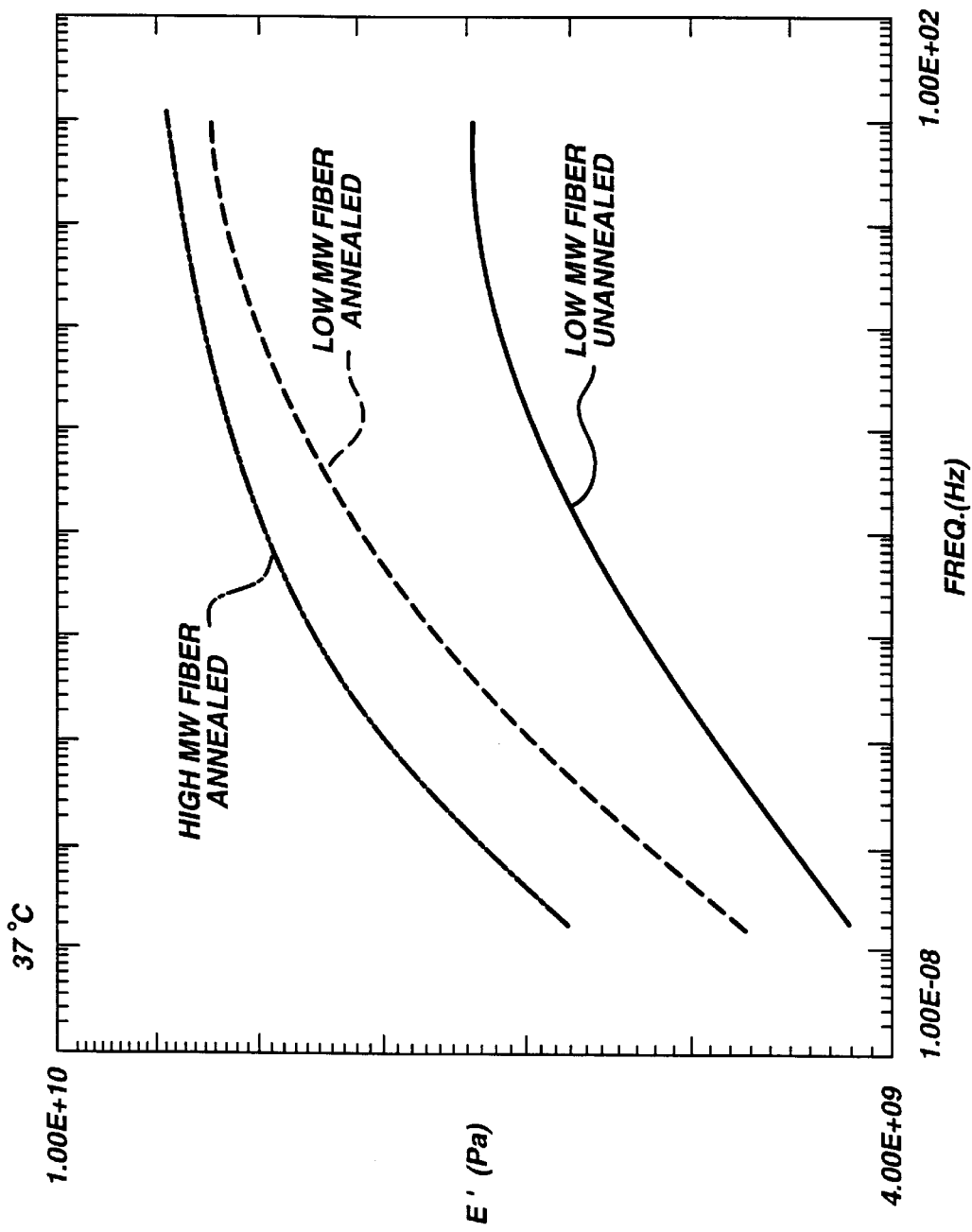
FIG. 2 is a graphical comparison of the tensile modulus of sutures produced by the inventive process compared to sutures produced by conventional processes.

The sutures were then individually tested on a DMS200 Dynamic Mechanical Spectrometer from Seiko Instruments to characterize the tensile modulus of the sutures. Each fiber was subjected to a sinusoidal oscillation and the mechanical response was measured. The instrument was set to auto-tension deformation mode with a 10 mm gauge length, a 2° C./min. heating rate beginning with an initial temperature of −150° C., ending at at a temperature of 170° C. and an initial force of 400 g. The modulus response versus temperature for all three sutures was determine at six different frequencies (0.5, 1, 2, 5, 10, and 20 Hz). The frequency multiplexing data obtained on the three fibers were used to generate a modulus response master curve based on the time-temperature superposition principle. Displayed in FIG. 2 are the modulus master curves obtained for the three sutures at 37° C. These curves may be used to assess the long-term properties of the sutures at this temperature. All three sutures show some change in the modulus response with respect to frequency or time, and these changes are significantly different for the three sutures.

The modulus master curves in FIG. 2 graphically illustrates that sutures produced in accordance with the inventive process have substantially improved mechanical properties as compared to the suture produced without annealing.

EXAMPLE 4

This example provides wide angle X-ray diffraction data on the suture samples that were made of the same resin and prepared similarly to samples (items #) described in Table 3 and 4. For example, sample 28 was prepared in the same manner as item 1 of Table 3. Similarly, sample 10 was prepared in the same manner as item 19; sample 12 in the same manner as item 21; sample 16 in the same manner as item 25; and sample 13 in the same manner as item 22. The details of the crystalline structure were determined by wide angle X-ray diffraction (WADX) and the data from these studies is presented in Table 5 below.

TABLE 5

WAXD TRANSMISSION 10/0 NYLON

| SAMPLE | Anneal Hours | Diam Microns | Crystal % | d 200 (A) | d 002 d 202 (A) | L 200 (A) | L002 (A) |
|---|---|---|---|---|---|---|---|
| 28 (6H) | 0 | 22.00 | 36 | 4.29 | 3.85 | 48 | 43 |
| 10 (6H) | 0 | 24.52 | 44 | 4.35 | 3.84 | 50 | 42 |
| 12 (6H) | 8 | 24.80 | 39 | 4.42 | 3.89 | 50 | 42 |
| 16 (6) | 4 | 23.36 | 33 | 4.48 | 3.94 | 45 | 39 |
| 13 (66) | 4 | 23.96 | 37 | 4.42 | 3.99 | 56 | 47 |

EXAMPLE 5

This example provides a comparison of the inventive suture to a commercially available polyamide suture.

The commercially produced monofilament suture was made of nylon 6 with a viscosity of about 1.5 and molecular weight of about 37,000. The properties of this suture were determined following the testing procedures specified in Example 2. The data from these tests is provided in Table 6 below (under the "Commercial Product" heading).

Size 10/0 suture was produced by the process described in Example 1 and annealed for 4 hours. The suture was made from a nylon 6 with a viscosity of about 1.775 and a weight average molecular weight of about 49,000. The physical properties of the inventive suture were determined as described in Example 2 and are presented in Table 6 below.

TABLE 6

| | Commercial Product | This Invention |
|---|---|---|
| SUTURE PROPERTIES | | |
| Suture size | 10/0 | 10/0 |
| Diameter (microns) | 24 | 24 |
| PRE-STERILIZATION | | |
| Tensile, Kpsi | 129 | 144 |

TABLE 6-continued

| | Commercial Product | This Invention |
|---|---|---|
| Knot, Kpsi | 106 | 108 |
| Elongation, % | 31.2 | 35.0 |
| POST STERILIZATION Co-60 | | |
| Tensile, Kpsi | 115 | 136 |
| Knot, Kpsi | 89 | 118 |
| Elongation, % | 28.9 | 32.0 |
| POST RESTERILIZATION ETO | | |
| Tensile, Kpsi | 111 | 136 |
| Knot, Kpsi | 81 | 108 |
| Elongation, % | 24.0 | 30.0 |

The data shows that the inventive suture has significantly improved properties as compared to the commercially available suture.

We claim:

1. An improved polyamide suture comprising a sterilized polyamide suture having a tensile strength of greater than 130 KPSI wherein the polyamide is selected from the group consisting of polyhexamethylene adipamide (nylon 66), polyhexamethylene sebacamide (nylon 610), polycapramide (nylon 6), polydodecanamide (nylon 12) and polyhexamethylene isophthalamide (nylon 61) and combinations of two or more thereof attached to a needle.

2. The suture of claim 1 wherein the polyamide is selected from the group consisting of polycapramide (nylon 6) and polyhexamethylene adipamide (nylon 66).

3. The suture of claim 2 wherein the polyamide has a weight average molecular weight of from about 48,000 to about 55,000.

4. The suture of claim 3 wherein the suture is a monofilament suture.

5. The suture of claim 4 wherein the suture has a diameter from in the range of from about 10 to about 69 microns.

6. The suture of claim 1 wherein the tensile strength of the suture is in the range of from about 132 KPSI to about 145 KPSI.

7. The suture of claim 1 wherein the tensile strength of the suture is in the range of from about 134 KPSI to about 145 KPSI.

8. A non-irritating polyamide suture suitable for use in animals comprising a sterilized polyamide suture having a tensile strength of greater than 130 KPSI wherein the polyamide is selected from the group consisting of polyhexamethylene adipamide (nylon 66), polyhexamethylene sebacamide (nylon 610), polycapramide (nylon 6), polydodecanamide (nylon 12) and polyhexamethylene isophthalamide (nylon 61) and combinations of two or more thereof attached to a needle.

* * * * *